United States Patent
Hoey et al.

(10) Patent No.: US 6,760,616 B2
(45) Date of Patent: Jul. 6, 2004

(54) TISSUE DISCRIMINATION AND APPLICATIONS IN MEDICAL PROCEDURES

(75) Inventors: Michael F. Hoey, Shoreview, MN (US); Corbett W. Stone, San Diego, CA (US); Kevin Foley, La Jolla, CA (US)

(73) Assignee: Nu Vasive, Inc., San Diego, CA (US)

( * ) Notice: Subject to any disclaimer, the term of this patent is extended or adjusted under 35 U.S.C. 154(b) by 0 days.

(21) Appl. No.: 09/860,648

(22) Filed: May 18, 2001

(65) Prior Publication Data

US 2002/0072686 A1 Jun. 13, 2002

Related U.S. Application Data

(60) Provisional application No. 60/205,634, filed on May 18, 2000, and provisional application No. 60/243,465, filed on Oct. 25, 2000.

(51) Int. Cl.[7] .................................................. A61B 5/05
(52) U.S. Cl. ........................................ 600/547; 600/554
(58) Field of Search ............................... 600/544, 546, 600/547, 548, 554, 587, 590, 594, 593; 607/72, 115–118, 145, 149, 150; 606/34, 41

(56) References Cited

U.S. PATENT DOCUMENTS

| | | | | |
|---|---|---|---|---|
| 4,962,766 A | * | 10/1990 | Herzon | 600/554 |
| 5,759,159 A | * | 6/1998 | Masreliez | 600/547 |
| 5,775,331 A | * | 7/1998 | Raymond et al. | 600/554 |
| 5,928,158 A | * | 7/1999 | Aristides | 600/547 |
| 6,135,965 A | * | 10/2000 | Tumer et al. | 600/476 |
| 6,292,701 B1 | * | 9/2001 | Prass et al. | 607/116 |
| 6,312,392 B1 | * | 11/2001 | Herzon | 600/554 |
| 6,466,817 B1 | * | 10/2002 | Kaula et al. | 600/546 |

* cited by examiner

*Primary Examiner*—Charles Marmor
(74) *Attorney, Agent, or Firm*—Jonathan Spangler

(57) ABSTRACT

A method and system for discriminating tissue types, controlling the level of therapy to tissue, and determining the health of a known tissue by measuring the characteristics an electrical signal applied to conductive element located within or by the tissue. Additionally, the method and system may be used for determining whether the conductive tip of a pedicle probe or pedicle screw is located in one of cortical bone, cancellous bone, and cortical bone near a boundary with soft tissue, whether the conductive tip of a cannula is located adjacent to one of nerve tissue and annulus tissue, and whether the conductive tip of a cathode is located adjacent to one of nerve tissue and prostate gland tissue.

24 Claims, 3 Drawing Sheets

TISSUE DISCRIMINATION AND APPLICATIONS IN MEDICAL PROCEDURES

CROSS-REFERENCES TO RELATED APPLICATIONS

This application claims the benefit of prior provisional application no. 60/205,634 filed May 18, 2000 and U.S. application Ser. No. 60/243,465 filed Oct. 25, 2000, under 37 CFR 1.78§(a)(3), the full disclosure of which is incorporated herein by reference.

TECHNICAL FIELD

The present invention is related to tissue surveillance systems.

BACKGROUND OF THE INVENTION

Systems and methods exist for determining when a probe, needle, catheter or other devices make contact with a particular tissue, e.g., U.S. Pat. No. 5,836,990 to Li entitled "Method and Apparatus for Determining Electrode/Tissue Contact". The Li patent teaches a method for determining when a catheter makes contact with tissue covered with an ionic liquid. The system measures the electrical impedance at a distal end of the catheter and determines tissue contact has been made when the impedance increases. The system does not identify the type of tissue contacted and presumes the tissue is covered in an ionic liquid. Accordingly, a need exists for a system and method that identify tissue and use this information in medical procedures.

Systems and method also exist for controlling the level of ablation of tissue. These systems monitor the impedance of tissue being ablated to determine if the ablation energy is optimal. The systems generally measure impedance to within approximately 20 ohms. These systems do not determine when sufficient therapy has been applied to the tissue and employ impedance measurement with low tolerance levels. Accordingly, a need exists for a system that may control any form of therapy by monitoring characteristics of an electrical signal applied to the tissue.

SUMMARY OF THE INVENTION

The present invention provides a system in which an electrical signal is applied to a tissue via electrodes disposed on a tissue probe. The electrical signal applied to the tissue preferably comprises a frequency variable current or voltage that is preferably applied to the tissue using a sliding frequency scale.

In accordance with the present invention, the response to the applied signal is measured as the signal passes through tissue disposed at, around, or adjacent to, the probe. The inventors have found that different tissue types display different electrical transmission properties, including different capacitance and impedance properties. Accordingly, by measuring the electrical characteristics of the response signal, it is possible to determine the type of tissue through which the signal is passing. Preferably, this is accomplished by comparison to known exemplary signal characteristics for various tissue types. Further, when the probe is known to be a first tissue, the system and method may determine when the probe is advanced into a different tissue based on the changed electrical characteristics of the signal applied the probe.

In accordance with the present invention, the electrical signal characteristics that are monitored may include the phase shift between the voltage and current passing through a selected tissue, and the impedance of the selected tissue. The present inventors have experimentally determined that these properties vary from one tissue type to another. In a preferred aspect of the present invention, the electrical signal applied to the tissue may be a sliding frequency signal so a frequency spectrum of phase shift and impedance of a tissue is determined, however, any electrical, magnetic, or optical signal whose phase relationship and impedance to passage through the tissue may be measured can be used.

In a preferred method, a probe is advanced to a position in, at, or adjacent to, a selected tissue and an electrical signal is applied to the tissue by an electrode on the probe. The response to this signal is then measured and compared against electrical, magnetic, or optical transmission characteristics for the various tissue types. For example, the present invention provides a method and system for determining whether the conductive tip of a pedicle probe or pedicle screw is located in one of cortical bone, cancellous bone, and cortical bone near a boundary with soft tissue, whether the conductive tip of a cannula is located adjacent to one of nerve tissue and annulus tissue, and whether the conductive tip of a cathode is located adjacent to one of nerve tissue and prostate gland tissue.

Further, the inventors have discovered that the signal transmission characteristics of various tissues vary as a function of the tissue's health. Accordingly, the present system can also be used to determine tissue health (for various tissue types) by comparing the signal responses of tissue (in response to stimulation by the probe) to responses for healthy tissue.

The present inventors have determined that different cell/tissue types exhibit different capacitive effects. In addition, these capacitive effects vary considerably between living and dead cells. Accordingly in another aspect of the invention, the present system discriminates between living and dead tissues. This feature of the invention is particularly useful when the present system is used in conjunction with a tissue ablation system. For instance, the tissue ablation system may be prevented from providing unnecessary energy to ablate tissue and thereby protect surrounding tissue.

Moreover, the present system can be adapted to sense the presence of a particular type(s) of tissue as the probe is advanced through the patient's body. Such a feature of the present invention is particularly advantageous when sensing for the presence of nerve tissue. Specifically, the probe can be advanced through the patient's body, with the response to the electrical stimulation emitted by the probe being continuously monitored such that as nerve tissue is approached; the response signal will begin to exhibit characteristics indicative of nerve tissue.

Such nerve sensing features of the present invention can be used, for example, to sense for the presence of spinal nerves when advancing surgical equipment (which may include cutting, drilling, screw insertion, implant, and tissue ablation systems) towards the patient's intervertebral space.

In an optional aspect of the present invention, a probe having an electrode positioned thereon is replaced with a probe, which is itself electrified. For example, an electrified needle or an electrified trocar or cannula can be used as the probe. An advantage of having the entire probe emit the signal (rather than just an electrode disposed thereon) is that the probe itself can be made to smaller dimensions, particularly in the case of an electrified needle.

In optional aspects of the present invention, the probe is mono-polar. Specifically, only a first electrode is disposed on the probe. A second electrode is then positioned some distance away from the first electrode at another location on the body. Alternately, the probe may be bi-polar with both the first and second electrodes positioned on the probe itself. Additionally, the probe may include a plurality of bi-polar electrodes placed along the probe (such as around the tip and the length of the probe) to determine tissue types around the probe.

In a preferred aspect of the present invention, the measurement of the phase angle relationship between the voltage and current of the signal and impedance of the signal may be used to determine: (1) the type of tissue in which the probe is located, (2) the health of the tissue, (3) the relative location of the tip of the probe (ie: in cases where the electrode is disposed in the tip of the probe); and (4) any combination of (1), (2) and (3). As such, by gathering data mapped by analyzing the response signal, measured characteristics can be used to correlate: (1) tissue identity, (2) tissue health, and (3) tissue location.

In addition, the present invention can be adapted to: (5) locate specific tissue within a body; (6) control application of therapy to tissue; (7) detect the state of health of tissue; (8) navigate to tissue; and (9) any combination of the above.

In one embodiment, the invention is a tissue system including a computer system having an analog to digital (A/D) converter and digital to analog (D/A) converter interface (PCI board), that may be used to generate the control signal which is applied to the electrode or conductive tip of the probe. The computer generates the signal via the D/A converter. Then the A/D converter converts the signal received from the conductive tip into digital samples by sampling the signal at a predetermined rate where the digital samples may have a fixed or variable number of bits and have linear, logarithmic or other scaling. The computer system determines characteristics of the received signal from the digital samples, in particular the phase angle and impedance at the conductive tip or other location of the probe where the electrode(s) may be located. Based on the determined characteristics taken over time (which is then stored in a knowledge base or tabulated form), the present invention may determine tissue identity and tissue location. In a preferred aspect, the electrode disposed on the probe comprises a bipolar electrode conductive tip probe.

In an optional aspect of the present invention, the application of therapy to the tissue in which the probe is located may be precisely controlled. Based on the characteristics of the tissue where the probe is located, tissue therapy application may be precisely controlled. For example, the application of heat or cooling therapy may be used to ablate or cool tissue. In one exemplary aspect, the same electrode(s) used for tissue discrimination (ie: determining tissue type for tissue disposed adjacent to the electrode on the probe) may also be used for tissue ablation by heating.

In various aspects, the level of heating or cooling of the tissue may be modulated as a function of the measured characteristics of the tissue. In particular, the phase angle and impedance of the tissue change as the tissue is heated or cooled to certain level. Accordingly, the application of therapy may be regulated by the present computer system. In particular, the computer system may communicate with a device applying therapy and automatically control the level of therapy.

Given that the present system can determine the type and location of various tissues within a patient, the present system may be used to determine the relative health of the tissue. In particular, the measured characteristics of the signal will vary for diseased or unhealthy tissue, as compared to normal healthy tissue. Thus, the present system may be used to determine the type of tissue, the location of the tissue, the health of tissue, and also to control therapy for tissue based on the same. Furthermore, the probe may optionally be coupled with an automated navigation system that navigates within the patient based on the measured characteristics of the received signal. Such a navigation system may use the tissue identity and location data to navigate to a particular location within an organ. Then the computer system may determine the health of the tissue at the location within the organ and control the application of therapy as appropriate.

As can be envisioned by one of skill in the art, many different combinations of the above may be used and accordingly the present invention is not limited by the scope of the appended claims.

In optional aspects of the invention, the characteristic electrical properties of the various tissue types are determined for different tissues at different RF frequencies. For example, the signal may be emitted from the probe (into the surrounding tissue) at frequencies in the range of 400 kHz to 100 MHz. Determining the electrical properties of various tissues at various signal frequencies may be advantageous in that different cell (ie: tissue) types may exhibit different harmonics. As such, tissues may be further characterized by measuring phase shift or impedance at various frequencies, or along a sliding frequency.

BRIEF DESCRIPTION OF THE FIGURES

Like reference numbers and designations in the various drawings indicate like elements.

BEST MODE OF CARRYING OUT THE INVENTION

Throughout this description, the preferred embodiment and examples shown should be considered as exemplars, rather than as limitations on the present invention.

Figure 1:
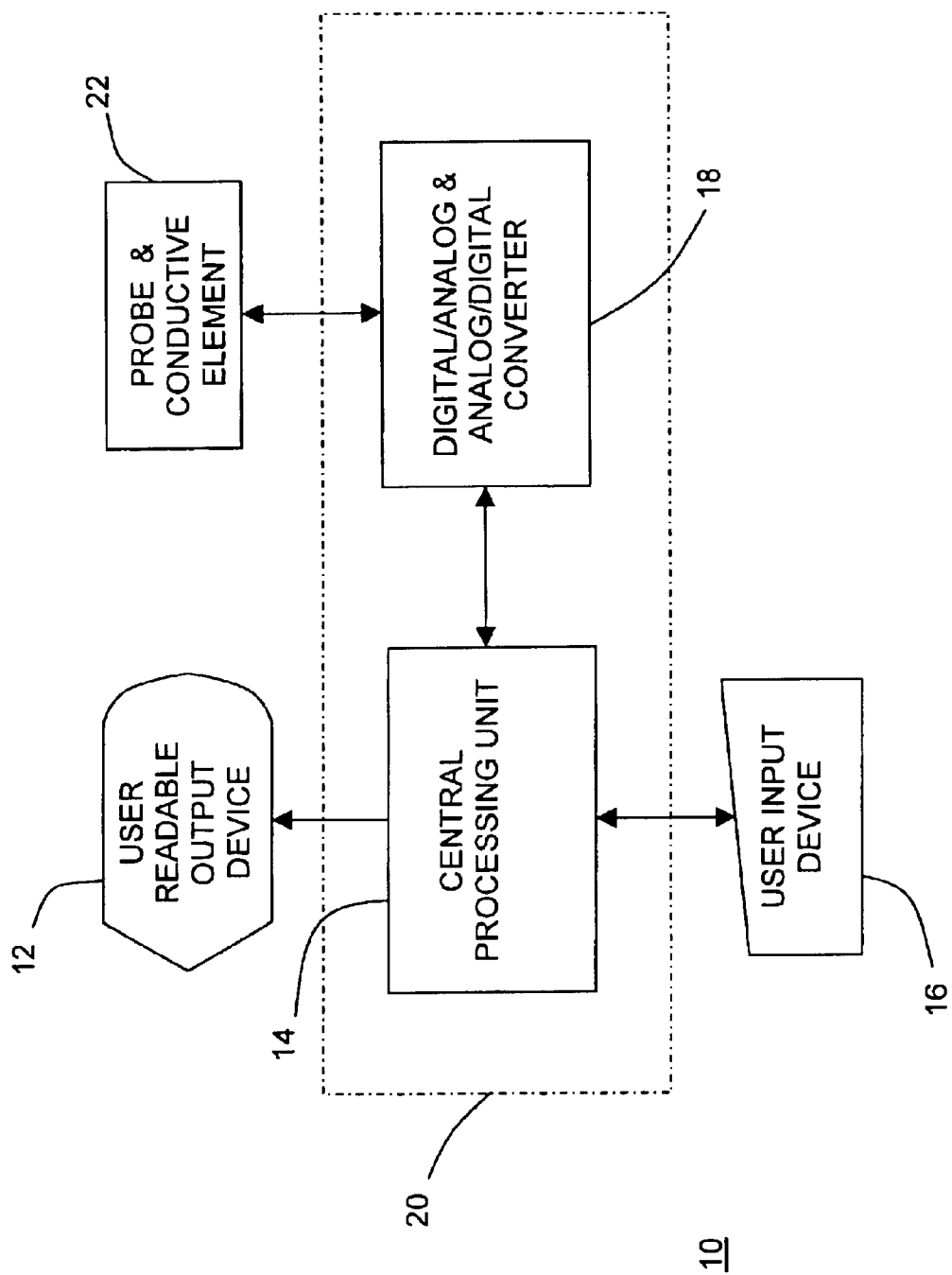
FIG. 1 is a block diagram of a tissue discrimination system in accordance with the present invention.

FIG. 1 is a diagram of tissue identification system 10 in accordance with the present invention. The system 10 includes a user readable output device 12, a user input device 16, a processor 20, and a probe 22. The processor 20 includes a central processing unit ("CPU") 14 and Digital to Analog converter ("D/A") and Analog to Digital Converter ("A/D") 18. The CPU 14 may be any microprocessor having sufficient processing power to control the operation of the D/A & A/D 18 and output device 12. The D/A & A/D 18 is any such device having a sufficient operating cycle to generate signals with the frequencies described herein and sufficient sampling rate to generate the digital samples described herein. The probe 22 is any medical device that may be used to hold one or more electrode thereon where the electrodes transmit and receive electrical signals. Exemplary probes include cannulae, needles, catheters, RF ablation devices, lasers, or other medical instruments. The probe 22 may have a single electrode (mono-polar), two electrodes (bipolar), or a plurality of electrodes (multi-polar) configuration. Throughout the remainder of the discussion, a probe with a conductive tip is discussed as one exemplary embodiment. It is understood that the electrodes could be placed anywhere along the circumference or width and length of the probe. A probe having multiple electrodes ideally includes groups of bipolar electrodes so the system or method of the invention may map the response of the electrode pairs.

The CPU 14 controls the operation of the D/A & A/D 18 and output device 12 based upon user selection received via the user input device 16. The user input device 16 may be any input device including a keyboard, mouse, or touch-sensitive screen. The output device may be any output device controllable by the CPU 14 such as computer monitor, printer, or other computer controlled display device. The system 10 generates an electrical signal that is transmitted to tissue near or about the probe 22. When the probe has an omni-directional conductive tip, the electrical signal may be propagated to a wide area of tissue about the conductive tip. The conductive tip may include an electrodes pair (bipolar) so that the electrical signal is directed primarily to tissue directly in the path of the probe's conductive tip (electrode pair). The system 10 provides an electrical signal at the electrode(s) on the probe via the D/A 18. In particular, the CPU generates a digital representation a signal to be transmitted by the probe 22. The D/A converts the digital signal to an analog signal that is transmitted through tissue by the probe 22.

The probe 22 also receives signals conducted by tissue surrounding the conductive tip of the probe 22. The A/D 18 converts the analog signal received by the electrode(s) of probe 22 into a digital signal that may be processed by the CPU 14.

In one embodiment, the system applies a fixed frequency signal to the probe electrode(s). In an exemplary embodiment the system 10 applies a signal to the probe's 22 electrode(s) having a frequency from 400 KHz to 100 MHz. The system 10 may apply a signal having a range or sliding frequency. The system 10 applies the RF signal to the electrode(s) via the CPU 14 and D/A 18.

The repeatable pattern of the applied signal may be any pattern where the phase of signal may be determined, i.e., any signal whose phase relationship (voltage to current) may be measured. In one embodiment, the applied signal is a sinusoidal signal. In another embodiment, the signal is a square wave signal where the phase of the signal is measured at a leading or a trailing edge of each square wave. Any signal whose phase relationship (voltage to current) may be measured can be used.

The A/D 18 converts signals received at the electrode(s) of the probe 22 to a digital signal for processing by the CPU 14. The CPU 14 determines characteristics of the tissue surrounding the probe's 22 electrodes by comparing the signal applied to the electrode(s) and the signal received from the same. In one embodiment the phase angle between voltage and current of the applied signal (effective capacitance) and impedance of the tissue surrounding the conductive element (electrode(s)) of the probe 22 is determined. I has been found that the measurement of the phase angle relationship and impedance may be used to determine the identity or type of tissue in which the probe electrode(s) is located, the relative health of the tissue, the relative location of the electrodes to other surrounding tissue, and to control the application of therapy to the tissue surrounding the probe's 22 electrode(s). In one embodiment, the measured characteristics may be used to determine the identity or type of tissue in which the probe electrode(s) is located, the relative health of the tissue, the relative location of the tip to other surrounding tissue, and to control the application of therapy to the tissue surrounding the probe's 22 electrode(s).

For example, the probe 22 may be placed in the kidney of a patient. Then, system 10 may apply a signal to the probe's 22 electrode(s) having a varying or fixed frequency. Then, the system 10 determines the phase angle and impedance of the signal applied to the probe 22 for each frequency of the signal. In one embodiment, the system 10 may use the combination of characteristics and frequency of the applied signal may be used to determine 1) that the electrode(s) of the probe is located within kidney tissue (identification of tissue) and 2) where within the kidney tissue is the probe located, i.e., near the outer cordial or inner medulla of the kidney (or more precisely) (specific identification of tissue).

The system 10 may also determine whether the kidney tissue about the electrode(s) of the probe 22 is healthy, i.e., ischemic, has tumors. By first knowing that the electrode(s) are in kidney tissue (a first tissue type), the system can look for changes in the signal characteristics to determine that unhealthy tissue (a second tissue type) is present within the kidney. When the system 10 determines that the tissue about the probe's 22 electrode(s) is not healthy, the system 10 may apply therapy to the tissue. The therapy may include the application of heat energy (ablation) or removal of heat energy (cryogenic cooling) of the tissue. The system 10 may continue to monitor characteristics of the tissue about the electrode(s) to determine when sufficient therapy has been applied. Then, when sufficient therapy has been applied, the system 10 may stop the application of therapy. In one embodiment, sufficient therapy has been applied when the tissue dies. The system 10 may then monitor the phase angle and impedance of the applied signal to determine when cell or tissue necrosis has occurred. The system 10 may also consider the frequency of the applied signal relative to the phase angle and impedance.

The A/D converter 18 converts the signal received from the electrode(s) into digital samples by sampling the signal at a predetermined rate where the digital samples may have a fixed or variable number of bits and have linear, logarithmic or other forms of scaling. The system 10 determines characteristics of the received signal from the digital samples, in particular the phase angle and impedance at the electrode(s). The system 10 may also include a knowledge base coupled to the CPU 14. The knowledge base may be stored characteristics about a large variety of know tissues. The base may also be correlated or indexed on the frequency of the applied signal. The knowledge base may be a database stored in fixed electronic medium (not shown) coupled to the CPU 14. In this embodiment, the CPU 14 compares the determined characteristics to characteristics stored in the database to determine tissue identity, location, health, and control the application of therapy. It is noted that the invention may also know the current position of the electrode(s), i.e., which tissue the electrode(s) are currently disposed therein. The knowledge base may further include information that correlates the known current position of electrode(s) (within a first tissue) with measured characteristics so the system may determine a second tissue type. Accordingly, the system or method of the invention may determine the tissue type of a second tissue based on knowledge of the position of the electrode(s) in a previous first tissue and measured characteristics of the signal applied to the electrode(s).

Figure 2:
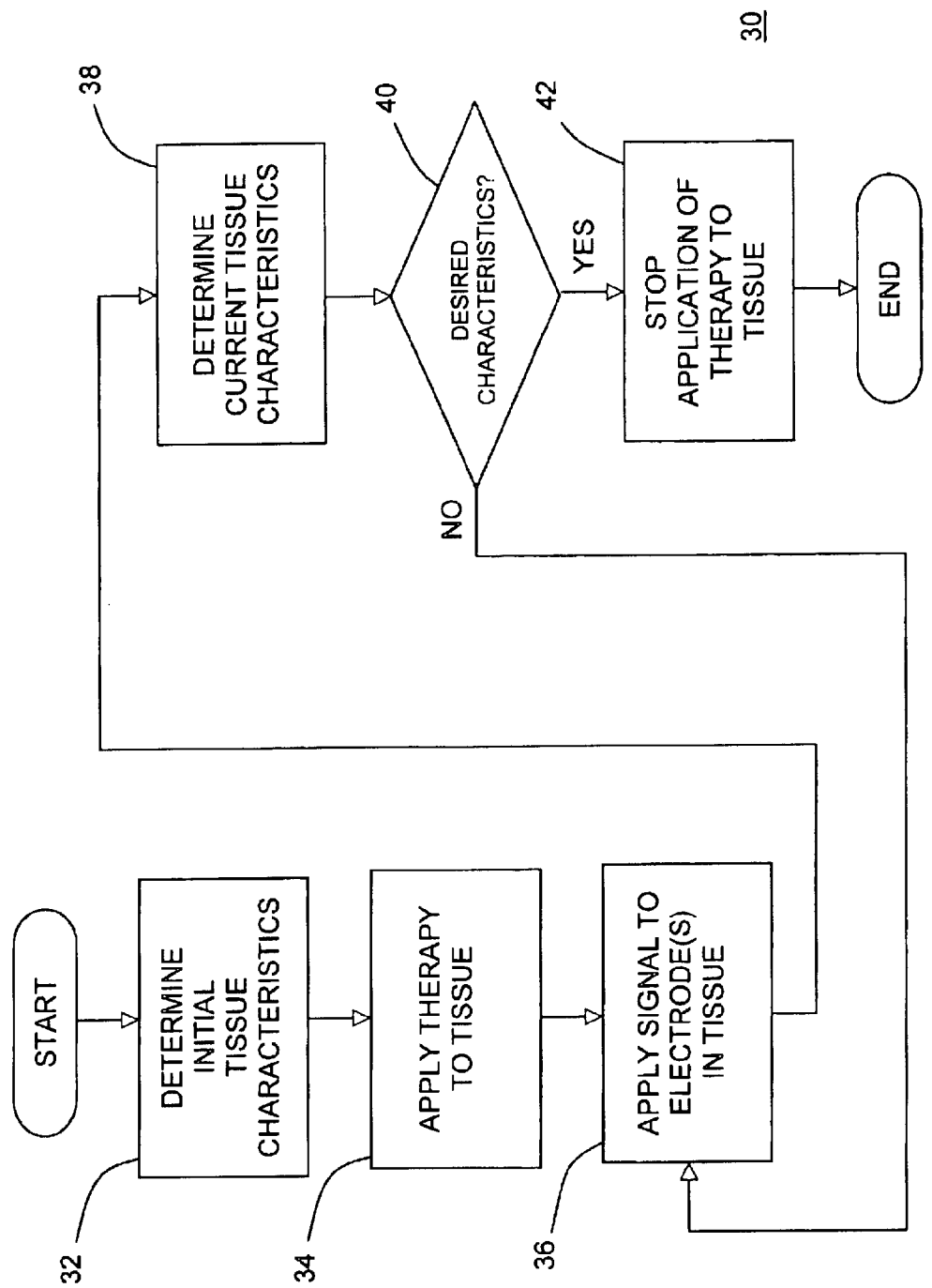
FIG. 2 illustrates a method of controlling the application of therapy to tissue according to the present invention.

It is noted that in another embodiment, that the present invention may be used with a device that automatically navigates through tissue. For example, the present invention may be coupled to an automated catheter system. The system 10 would provide tissue identity and location to the navigation system so the navigation system may navigate to a desired location. Once at the desired location, the system 10 may determine the health of the tissue. Then, the system 10 may control the application of therapy to the tissue based on the determined health of the tissue. For example, a navigation system in conjunction with system 10 may direct the probe to a specific location within kidney tissue. Based on the known characteristics of the tissue, the health of the tissue may be determined and the application of therapy may be applied when needed. A method 30 of applying therapy is shown in FIG. 2. In step 32, the method first determines the initial characteristics of the tissue. Then therapy is applied to the tissue (step 34). Therapy for the kidney tissue may include the application of heat or cooling therapy to ablate or cool the tissue. The level of heating or cooling of the tissue may be modulated as a function of the measured characteristics of the tissue. In particular, the phase angle and impedance of the tissue will change as the tissue is heated or cooled to a certain level. The method applies a signal to electrode(s) in the tissue receiving therapy (step 36). The method then determines the current tissue characteristics based on the applied signal (step 38). When the desired tissue characteristics (sufficient therapy applied) (step 40), the method stops the application of therapy to the tissue (step 42). If, on the other hand, the desired tissue characteristics are not achieved the method returns to the step of applying signal to electrode(s) in tissue (step 36) and again progresses through the remaining steps. Accordingly, the application of therapy may be regulated by the system 10. In one embodiment, the system 10 communicates with a device applying therapy and automatically controls the level of therapy.

Figure 3:
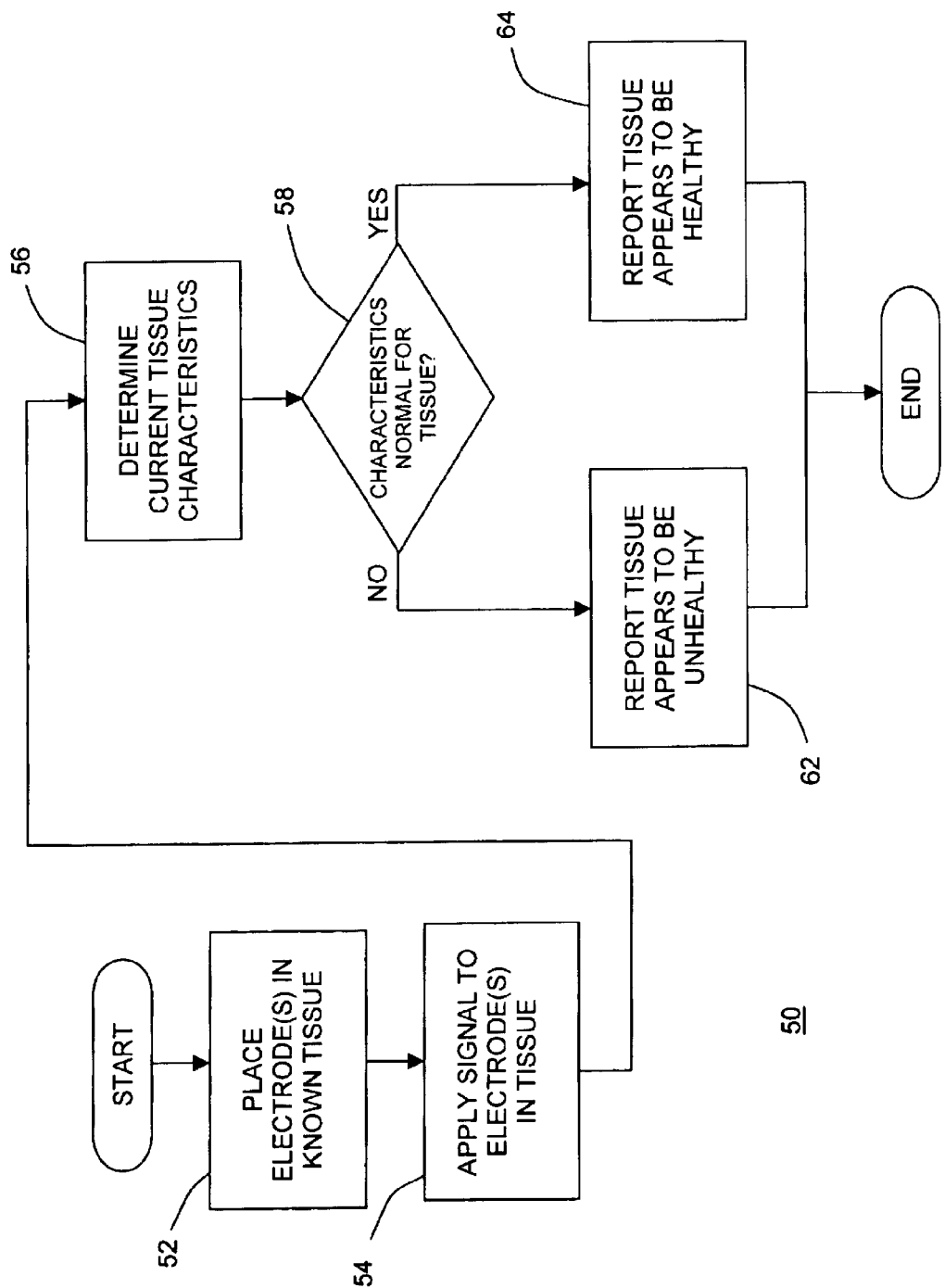
FIG. 3 illustrates a method of determining tissue health according to the present invention.

As noted, the system 10 may be used to determine the relative health of the tissue. The measured characteristics of the signal will vary for diseased or unhealthy tissue. For example, it has been found that cancerous cells have measurably different impedance from healthy tissue. FIG. 3 illustrates a method 50 of determining tissue health according to the present invention. The method places the electrode (s) in known tissue (step 52). The tissue may be known by first determining the location of the electrode(s) using techniques described above. Then the method applies a signal to the electrode(s) in the tissue of interest (step 54). The signal may be a signal of varying frequency, e.g., a sliding frequency signal in one embodiment. The method or system then determines the tissue characteristics based on the applied signal (step 56). The determined characteristics are compared to normal or expected characteristics for healthy or normal known tissue (step 58). When the determined characteristics are different from the expected characteristics for the known tissue (when healthy) (by some tolerance amount), the method or system indicates that the tissue at the electrode(s) is unhealthy (62). The method may also indicate what type of disease the tissue may have based on known characteristics of diseased tissue, i.e., tissue appears to be cancerous or ischemic. Otherwise, the system may report that the tissue near the electrode(s) appears to be healthy (64).

In another embodiment, the probe 22 may be a pedicle screw or pedicle probe. During the insertion of a pedicle screw, it is critical that the pedicle wall is not violated. Surgeons use image intensifiers and other equipment to prevent such a violation. The tissue discrimination system of the present invention may be used to monitor the position of the pedicle probe or pedicle screw. In particular the system monitors the impedance and capacitance or phase shift at the tip of the pedicle probe or screw to determine whether the tip is in cortical bone, cancellous bone, or cortical bone near a boundary with soft tissue.

In this embodiment, the outer surface of the pedicle screw may be non-conductive except to the head and tip of the pedicle screw. Likewise, the outer surface of the pedicle probe is non-conductive except for the distal and proximal ends of the probe. A conductive lead is then applied to the head of the pedicle screw or proximal end of the pedicle probe to conduct a signal to the tip of the screw or probe, the signal having a varying or fixed frequency.

Then, the system 10 determines the phase angle and impedance of the signal applied to the tip for each frequency of the signal. The system 10 uses the combination of characteristics and frequency of the applied signal may be used to determine whether the tip is located in cortical bone, cancellous bone, or cortical bone near the boundary with soft tissue. Depending on the determination, the surgeon may continue the insertion of the pedicle probe or screw.

In another embodiment, the probe 22 may be a cannula to be inserted adjacent to an annulus of a patient's spinal disc prior to performing an annulotomy. During the insertion of the cannula towards the annulus, it is critical that the cannula not rest again a nerve along side the annulus wall. Surgeons use electromyography (EMG) equipment and other equipment to prevent such a situation. The tissue discrimination system 10 of the present invention may be used to monitor the position of the cannula as it is advanced to the annulus wall. In particular, the system monitors the impedance and capacitance or phase shift at the tip of the cannula to determine whether the distal tip is adjacent to nerve tissue or annulus tissue.

In this embodiment, the outer surface of the cannula is non-conductive except for the distal and proximal ends of the cannula. A conductive lead is then applied to the proximal end of the cannula to conduct a signal to the tip of cannula, the signal having a varying or fixed frequency.

Then, the system 10 determines the phase angle and impedance of the signal applied to the tip for each frequency of the signal. The system 10 uses the combination of characteristics and frequency of the applied signal may be used to determine whether the tip is located adjacent to nerve tissue or annulus tissue. Depending on the determination, the surgeon may continue the insertion of the cannula.

In another embodiment, the probe 22 may be an ablation cathode to be inserted into a patient's prostate gland prior to performing prostate gland ablation. During the insertion of the cathode into the prostate gland, it is critical that the cathode is not near or adjacent to nerve tissue along side or within the prostate gland. Surgeons use image intensifier equipment and other equipment to prevent such a situation. The tissue discrimination system 10 of the present invention may be used to monitor the position of the cathode as it is advanced into the prostate gland. In particular, the system monitors the impedance and capacitance or phase shift at the tip of the cathode to determine whether the distal tip is adjacent to nerve tissue or prostate gland tissue.

In this embodiment, the signal is applied to the ablation cathode tip, the signal having a varying or fixed frequency. Then, the system 10 determines the phase angle and impedance of the signal applied to the tip for each frequency of the signal. The system 10 uses the combination of characteristics and frequency of the applied signal may be used to determine whether the tip is located adjacent to nerve tissue or prostate gland tissue. Depending on the determination, the surgeon may continue the insertion of the cathode.

While this invention has been described in terms of a best mode for achieving this invention's objectives, it will be appreciated by those skilled in the art that variations may be accomplished in view of these teachings without deviating from the spirit or scope of the present invention. For example, the present invention may be implemented using any combination of computer programming software, firmware or hardware. As a preparatory step to practicing the invention or constructing an apparatus according to the invention, the computer programming code (whether software or firmware) according to the invention will typically be stored in one or more machine readable storage mediums such as fixed (hard) drives, diskettes, optical disks, magnetic tape, semiconductor memories such as ROMs, PROMs, etc., thereby making an article of manufacture in accordance with the invention. The article of manufacture containing the computer programming code is used by either executing the code directly from the storage device, by copying the code from the storage device into another storage device such as a hard disk, RAM, etc. or by transmitting the code on a network for remote execution.

As can be envisioned by one of skill in the art, many different combinations of the above may be used and accordingly the present invention is not limited by the scope of the appended claims.

What is claimed is:

1. A method of determining whether a conductive element of a probe is located adjacent to a characterized body tissue comprising the steps of:
   a) applying an electrical signal to the conductive element;
   b) determining characteristics of the applied signal, including a phase angle; and
   c) determining whether the conductive element of a probe is located adjacent to a characterized body tissue based on the phase angle of the applied signal, wherein said characterized body tissue comprises one of nerve tissue, prostate gland tissue, and annulus tissue.

2. The method of claim 1, wherein the determined characteristics of the applied signal include an impedance of the applied signal through the tissue.

3. The method of claim 1, wherein the probe comprises one of a cannula and a cathode.

4. The method of claim 1, wherein step a) applies signals having a range of predetermined frequencies to the conductive element.

5. The method of claim 1, wherein step a) includes determining whether the conductive element of a probe is located adjacent to a said tissue based on the determined characteristics and frequency of the resulting signal.

6. The method of claim 1, wherein the conductive element is an electrode.

7. The method of claim 1, wherein the conductive element includes a pair of electrodes and the signal is passed between said electrodes.

8. The method of claim 1, wherein the signal is an electrical signal having a sliding frequency.

9. An article of manufacture for use in determining whether a conductive element of a probe is located adjacent to a characterized body tissue, the article of manufacture comprising computer readable storage media including program logic embedded therein that causes control circuitry to perform the steps:
   a) applying a signal to the conductive element;
   b) determining characteristics of the applied signal, including a phase angle; and
   c) determining whether the conductive element of a probe is located adjacent to a characterized tissue based on the phase angle of the applied signal, wherein said characterized body tissue comprises one of nerve tissue, prostate gland tissue, and annulus tissue.

10. The article of manufacture of claim 9, wherein the determined characteristics of the applied signal further include an impedance of the applied signal through the tissue.

11. The article of manufacture of claim 9, wherein the probe comprises one of a cannula and a cathode.

12. The article of manufacture of claim 9, wherein step a) applies signals having a range of predetermined frequencies to the conductive element.

13. The article of manufacture of claim 9, wherein step c) includes determining whether the conductive element of a probe is located adjacent to said tissue based on the determined characteristics and frequency of the resulting signal.

14. The article of manufacture of claim 9, wherein the conductive element is an electrode.

15. The article of manufacture of claim 9, wherein the conductive element includes a pair of electrodes and the signal is passed between said electrodes.

16. The article of manufacture of claim 9, wherein the signal is an electrical signal having a sliding frequency.

17. An apparatus for use in determining whether a conductive element of a probe is located adjacent to a characterized body tissue, the apparatus including:
   a) means for applying a signal to the conductive element;
   b) means for determining characteristics of the applied signal, including a phase angle of the applied signal; and
   c) means for determining whether the conductive element of a probe is located adjacent to a characterized body tissue based on the phase angle of the applied signal, wherein said characterized body tissue comprises one of nerve tissue, prostate gland tissue, and annulus tissue.

18. The apparatus of claim 17, wherein the determined characteristics of the applied signal include an impedance of the applied signal through the tissue.

19. The apparatus of claim 17, wherein means for applying a signal includes means for applying signals having a range of predetermined frequencies to the conductive element.

20. The apparatus of claim 17, wherein the means for determining whether the conductive element of a probe is located adjacent to a said tissue includes means for determining whether the conductive element of a probe is located adjacent to said tissue based on the determined characteristics and frequency of the signal.

21. The apparatus of claim 17, wherein the conductive element is an electrode.

22. The apparatus of claim 17, wherein the conductive element includes a pair of electrodes and the signal is passed between said electrodes.

23. The apparatus of claim 17, wherein the signal is an electrical signal having a sliding frequency.

24. The apparatus of claim 17, wherein the probe comprises one of a cannula and a cathode.

* * * * *